United States Patent [19]

Hironaka et al.

[11] Patent Number: 4,551,555

[45] Date of Patent: Nov. 5, 1985

[54] PROCESS FOR THE PRODUCTION OF CARBONYL COMPOUNDS

[75] Inventors: Yoshio Hironaka, Sodegaura; Takashi Kumazawa, Kisarazu, both of Japan

[73] Assignee: Idemitsu Kosan Company Limited, Tokyo, Japan

[21] Appl. No.: 616,594

[22] Filed: Jun. 1, 1984

[30] Foreign Application Priority Data

Jun. 15, 1983 [JP] Japan ................... 58-105945

[51] Int. Cl.$^4$ ........................................... C07C 45/35
[52] U.S. Cl. ................................. 568/401; 568/360
[58] Field of Search ............................ 568/401, 360

[56] References Cited

U.S. PATENT DOCUMENTS

| | | | |
|---|---|---|---|
| 3,119,874 | 1/1964 | Paszthory et al. | 568/401 |
| 3,131,223 | 4/1964 | Smidt et al. | 568/401 |
| 3,154,586 | 10/1964 | Bänder et al. | 568/401 |
| 3,529,020 | 9/1970 | Landis | 568/360 |
| 4,195,039 | 3/1980 | Mimoun et al. | 568/401 |

*Primary Examiner*—James H. Reamer
*Attorney, Agent, or Firm*—Frishauf, Holtz, Goodman & Woodward

[57] ABSTRACT

In the process for producing a carbonyl compound by contacting olefin and oxygen or oxygen-containing gas with a catalyst in the presence of water, a catalyst comprising a carrier and (a) rhodium, (b) manganese and (c) at least one of the Group IIIA elements (excluding an actinium series elements) is used. Also, the catalyst further containing zinc compounds as the component (d) is used.

According to this invention, the selectivity and the conversion of carbonyl compound such as methyl ethyl ketone are highly improved, and halogenated compounds are not produced.

25 Claims, No Drawings

PROCESS FOR THE PRODUCTION OF CARBONYL COMPOUNDS

BACKGROUND OF THE INVENTION

For the production of carbonyl compounds through oxidation of olefins, the Hoechst-Wacker process is well known (see, Japanese Patent Publication No. 7869/1961). Palladium chloride/copper chloride-base catalyst out of Wacker type catalysts as used in the Hoechst-Wacker process are of high activity and used in oxidation of ethylene or propylene. These catalysts, however, have a disadvantage in that when used in oxidation of olefins containing 4 or more carbon atoms, they are liable to yield chlorinated compounds. In addition, catalysts comprising palladium (Pd) and one or more elements such as iron (Fe), cobalt (Co), nickel (Ni), manganese (Mn), etc. are known (see, Japanese Patent Publication No. 6643/1976 and Japanese Patent Application Laid-Open No. 43686/1978). These catalysts are capable of suppressing the formation of halogenated compounds as described above but have a disadvantage of being inferior in activity.

In order to overcome such problems of the prior art, the present inventors have already proposed a catalyst having rhodium and manganese supported on a carrier (Japanese Patent Application No. 177551/1982). This catalyst, however, is not sufficiently satisfactory in that the selectivity of the desired carbonyl compound is somewhat low.

The present invention is therefore intended to provide more improved catalyst compositions for use in oxidation of olefins. As a result of further investigations, it has been found that when there are employed novel catalysts comprising rhodium, manganese, and at least one of the Group IIIA elements (excluding the actinium series elements) of the Periodic Table, the selectivity of the desired carbonyl compound, particularly methyl ethyl ketone is markedly increased and undesirable chlorinated compounds are not produced. It has further been found that addition of zinc compounds to the above-described catalyst compositions enables to increase the durability or the life time of the resulting catalysts.

SUMMARY OF THE INVENTION

An object of the invention is to provide a process for efficiently producing carbonyl compounds through oxidation of olefins.

Another object of the invention is to provide novel catalyst compositions for use in oxidation of olefins.

It has been found that the objects are attained by adding at least one of the Group IIIA elements (excluding the actinium series elements) and, if desired, further zinc compounds to rhodium and manganese.

The present invention relates to a process for producing carbonyl compounds by contacting olefins and oxygen or oxygen-containing gas with a catalyst in the presence of water, which process is characterized by that the catalyst comprises a carrier supported thereon (a) rhodium, (b) manganese, (c) at least one of the Group IIIA elements (excluding the actinium series elements), or further (d) zinc compounds.

DETAILED DESCRIPTION OF THE INVENTION

The catalyst of the present invention, in one embodiment, comprises a carrier and (a) rhodium, (b) manganese and (c) at least one of the Group IIIA elements (excluding the actinium series elements). In another embodiment, it comprises a carrier and (a) rhodium, (b) manganese, (c) at least one of the Group IIIA elements (excluding the actinium series elements), and (d) zinc compounds.

For the component (a), various rhodium compounds can be used as starting materials. Preferred are those rhodium compounds which are easily soluble in water, alcohols, etc. Examples include halides, sulfates, nitrates, chlorates, acetates, monochloroacetates, oxides, and hydroxides. Of these compounds, rhodium halides, particularly rhodium chloride are preferred. The amount of the component (a) supported on the carrier is usually from 0.2 to 5 parts by weight (calculated as the rhodium element) per 100 parts by weight of the carrier.

Also for the component (b), various manganese compounds can be used as starting materials. Water-soluble manganese compounds are preferred. Examples include halides, sulfates, nitrates, carbonates, acetates, oxalates, and hydroxides. Of these compounds, manganese halides, particularly manganese chloride are preferred. The amount of the component (b) supported on the carrier is usually from 0.5 to 30 parts by weight (calculated as the manganese element) per 100 parts by weight of the carrier.

In one embodiment of the present invention, as described above, at least one of the Group IIIA elements (excluding the atinium series elements) is used as the component (c) with the components (a) and (b) as described above. The Group IIIA elements include, as well as yttrium (Y) and scandium (Sc), the lanthanum series elements, i.e., lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). Of these, yttrium, praseodymium, neodymium, gadolinium, holmium, erbium and ytterbium are preferred. Their chlorides are especially preferred. The amount of the component (c) supported on the carrier is usually from 0.1 to 30 parts by weight (calculated as the corresponding element) per 100 parts by weight of the carrier.

In another embodiment of the present invention, zinc compounds are added as the component (d) with the components (a), (b) and (c). As these zinc compounds, water-soluble ones are preferred. Examples include halides, nitrates, sulfates, carbonates, acetates, oxalates, and hydroxides. The amount of the component (d) supported on the carrier is usually from 0.5 to 10 parts by weight (calculated as the zinc element) per 100 perts by weight of the carrier.

Carriers for the catalyst of the present invention include silica, alumina, silica/alumina, zeolite, and activated carbon. Of these compounds, $\gamma$-alumina is preferred. Particularly preferred is $\gamma$-alumina previously treated with hydrochloric acid.

The components (a) to (d) can be deposited on the carrier in any suitable manner such as by the impregnation method and the adsorption method which are commonly used in deposition of metal components. In addition, a method can be employed in which aqueous solution of the components and a carrier in a colloidal form are mixed, concentrated, solidified and then molded. Deposition can be carried out in the single step or a series of steps.

The carrier with the components (a) to (d) supported thereon is then dried and subsequently calcined at a temperature of from 80° to 400° C., preferably from 100° to 250° C. in air or gases such as inert gases (e.g., nitrogen, argon, etc.) and chlorine gas for a period of from 0 to 10 hours, preferably from 3 to 6 hours, whereupon the desired catalyst of high activity and high stability can be obtained.

On contacting olefins and oxygen or oxygen-containing gas with the catalyst of the present invention, the corresponding carbonyl compounds can be efficiently obtained.

Olefins which can be used in the present invention include aliphatic straight-chain olefins such as ethylene, propylene, butene-1, butene-2 and n-hexene; branched aliphatic olefins such as 3-methylbutene-1 and 3-methylpentene-1; diolefins such as 1,3-butadiene and cyclohexadiene; and alicyclic olefins such as cyclopentene and cyclohexene. Mixtures of butene-1, butene-2, etc. can also be used. The olefin feedstock may contain minor proportions of saturated hydrocarbons such as n-butane and isobutane or nitrogen, etc.

In producing carbonyl compounds from olefins, the olefin feedstock is mixed with oxygen or an oxygen-containing gas and then contacted with the catalyst in the presence of water (usually vaporized water) at a temperature of from 50° to 300° C., preferably from 100° to 250° C. under a pressure of from 0 to 50 kilograms per square centimeter (gauge), preferably from 0 to 10 kilograms per square centimeter (gauge). This reaction can be carried out in any of the fixed-bed, fluidized-bed, and transferred-bed systems and by any of the gas phase process, gas/liquid mixed phase process, and liquid phase process. It is preferred for the reaction to be performed in a flow-type system by the gas phase process. It is particularly preferred to employ the gas phase reaction from a viewpoint of separation and purification of the product. As the oxygen-containing gas, as well as air, a mixed gas of oxygen and an inert gas (e.g., nitrogen) and the like are suitable to use. It is desirable that water is vaporized by passing through a pre-heating layer and then introduced as steam into the reaction system.

The proportions of the olefin, oxygen or oxygen-containing gas and water should be determined taking into account the type of the olefin, the reaction conditions, and so forth. In general, the suitable volume ratio of olefin:oxygen or oxygen-containing gas: water (as vaporized state) is 1:0.5–40:1–40. The contact time between the mixture and the catalyst is usually from 0.1 to 20 seconds and preferably from 1 to 10 seconds.

In accordance with the present invention, useful carbonyl compounds such as acetaldehyde, acetone, methyl ethyl ketone, methyl vinyl ketone, and crotonaldehyde can be efficiently produced from the corresponding olefins. One of the major features of the present invention is that methyl ethyl ketone can be obtained in high yield from low reactivity olefins such as butene-1 and butene-2. In the production of methyl ethyl ketone from butenes, the selectivity and the conversion are high and, furthermore, halogenated compounds such as chlorides are not produced. Thus the equipment is free from corrosion. Further in view of the fact that the strength and stability of the catalyst are sufficiently satisfactory, the process of the present invention is very useful for industrial use.

The present invention is described in detail with reference to the following examples.

EXAMPLE 1

A mixture of 9.73 grams of manganese chloride ($MnCl_2 \cdot 4H_2O$), 0.99 gram of rhodium chloride ($RhCl_3 \cdot 3H_2O$), and 0.89 gram of holmium chloride ($HoCl_3 \cdot 6H_2O$) was dissolved in 60 milliliters of distilled water. A γ-alumina carrier molded (specific surface area: 200 square meter per gram; size: 3 millimeters (diameter)×3 millimeters (length)) (38.6 grams) was impregnated with the above-prepared solution which was then vaporized to dryness. The carrier was heated at 250° C. for 4 hours in flowing air. There was thus obtained a catalyst supporting 1 part by weight of rhodium, 7 parts by weight of manganese, and 1 part by weight of holmium per 100 parts by weight of the carrier.

Twenty milliliters of the above-prepared catalyst was packed into a stainless steel reaction tube (inner diameter: 25 millimeters), through which a mixed gas consisting of 7.5% by volume of butene-1, 7.5% by volume of oxygen, 15% by volume of nitrogen, and 70% by volume of steam was passed under conditions of temperature 180° C., pressure 3 kilograms per square centimeter (gauge), and contact time 1.5 seconds, whereupon butene-1 was oxidized. The results are shown in Table 1.

The butene-1 conversion, the methyl ethyl ketone selectivity, and the methyl ethyl ketone yield were calculated as follows:

Conversion (mole %) =

$$\frac{\text{(Number of moles of butene-1 fed)} - \text{(Number of moles of butene-1 recovered)}}{\text{(Number of moles of butene-1 fed)}} \times 100$$

Selectivity (mole %) =

$$\frac{\text{(Number of moles of methyl ethyl ketone formed)}}{\text{(Number of moles of butene-1 fed)} - \text{(Number of moles of butene-1 recovered)}} \times 100$$

Yield (mole %) =

$$\frac{\text{(Number of moles of methyl ethyl ketone formed)}}{\text{(Number of moles of butene-1 fed)}} \times 100$$

Gas chromatography analysis of the product confirmed that no chlorinated compound was formed.

EXAMPLE 2

The procedure of Example 1 was repeated wherein 0.864 gram of ytterbium chloride ($YbCl_3 \cdot 6H_2O$) was used in place of holmium chloride. The results are shown in Table 1.

EXAMPLE 3

The procedure of Example 1 was repeated wherein 0.88 gram of erbium chloride ($ErCl_3 \cdot 6H_2O$) was used in place of holmium chloride. The results are shown in Table 1.

EXAMPLE 4

The procedure of Example 1 was repeated wherein 1.02 grams of praseodymium chloride ($PrCl_3 \cdot 7H_2O$) was used in place of holmium chloride. The results are shown in Table 1.

EXAMPLE 5

The procedure of Example 1 was repeated wherein 1.32 grams of yttrium chloride (YCl$_3$·6H$_2$O) was used in place of holmium chloride. The results are shown in Table 1.

EXAMPLE 6

The procedure of Example 1 was repeated wherein 0.96 gram of neodymium chloride (NdCl$_3$·6H$_2$O) was used in place of holmium chloride. The results are shown in Table 1.

EXAMPLE 7

The procedure of Example 1 was repeated wherein 0.87 gram of gadolinium chloride (GdCl$_3$·6H$_2$O) was used in place of holmium chloride. The results are shown in Table 1.

EXAMPLE 8

The procedure of Example 1 was repeated except that the amount of holmium chloride used was changed to 0.445 gram, and γ-alumina which was impregnated with 250 milliliters of 2 normal hydrogen chloride (2N HCl) for 4 hours, recovered by filtration, washed three times with distilled water, and the dried, was used as the catalyst. The results are shown in Table 1.

EXAMPLE 9

The procedure of Example 2 was repeated wherein the amount of ytterbium chloride was changed to 0.432 gram. The results are shown in Table 1.

EXAMPLE 10

The procedure of Example 2 was repeated wherein the amount of manganese chloride was changed to 6.95 grams, and the heat treatment in the preparation of the catalyst was performed at a temperature of 200° C. The results are shown in Table 1.

EXAMPLE 11

The procedure of Example 1 was repeated wherein the amount of manganese chloride was changed to 6.95 grams, and the alumina carrier was calcined at 900° C. for 4 hours. The results are shown in Table 1.

EXAMPLE 12

The procedure of Example 1 was repeated wherein 0.87 gram of ytterbium sulfate (YbSO$_4$·8H$_2$O) was used in place of holmium chloride. The results are shown in Table 1.

COMPARATIVE EXAMPLE 1

The procedure of Example 1 was repeated wherein holmium chloride was not used. The results are shown in Table 1.

COMPARATIVE EXAMPLE 2

The procedure of Example 1 was repeated wherein the amount of manganese chloride was changed to 6.95 grams and holmium chloride was not used. The results are shown in Table 1.

TABLE 1

| Run No. | Amounts of Metals Deposited* | Butene-1 Conversion (mol %) | Methyl Ethyl Ketone Selectivity (mol %) | Methyl Ethyl Ketone Yield (mol %) |
|---|---|---|---|---|
| Example 1 | Rh:Mn:Ho = 1:7:1 | 61 | 75 | 46 |
| Example 2 | Rh:Mn:Yb = 1:7:1 | 59 | 90 | 53 |
| Example 3 | Rh:Mn:Er = 1:7:1 | 64 | 76 | 48 |
| Example 4 | Rh:Mn:Pr = 1:7:1 | 71 | 80 | 57 |
| Example 5 | Rh:Mn:Y = 1:7:1 | 52 | 85 | 44 |
| Example 6 | Rh:Mn:Nd = 1:7:1 | 55 | 92 | 50 |
| Example 7 | Rh:Mn:Gd = 1:7:1 | 58 | 86 | 50 |
| Example 8 | Rh:Mn:Ho = 1:7:0.5 | 57 | 90 | 51 |
| Example 9 | Rh:Mn:Yb = 1:7:0.5 | 63 | 76 | 48 |
| Example 10 | Rh:Mn:Yb = 1:5:1 | 61 | 83 | 51 |
| Example 11 | Rh:Mn:Ho = 1:5:1 | 51 | 88 | 44 |
| Example 12 | Rh:Mn:Yb = 1:7:1 | 52 | 84 | 44 |
| Comparative Example 1 | Rh:Mn = 1:7 | 62 | 68 | 42 |
| Comparative Example 2 | Rh:Mn = 1:5 | 66 | 66 | 43 |

*Amounts of metals deposited per 100 parts by weight of the carrier (parts by weight)

EXAMPLE 13

A mixture of 9.73 grams of manganese chloride (MnCl$_2$·4H$_2$O), 0.99 gram of rhodium chloride (RhCl$_3$·3H$_2$O) and 1.73 grams of ytterbium chloride (YbCl$_3$·6H$_2$O) was dissolved in 60 milliliters of water. A γ-alumina carrier molded (specific surface area: 200 square meters per gram; size: 3 millimeters (diameter)×3 millimeters (length)) (38.6 grams) was impregnated with the above-prepared solution which was then vaporized to dryness. The carrier was then heated at 200° C. for 6 hours in flowing air. There was thus obtained a catalyst supporting 1 part by weight of rhodium, 7 parts by weight of manganese, and 2 parts by weight of ytterbium per 100 parts by weight of the carrier.

Twenty milliliters of the above-prepared catalyst was packed into a stainless steel reaction tube (inner diameter: 25 millimeters), through which a mixed gas consisting of 7.5% by volume of cis-butene-2, 7.5% by volume of oxygen, 50% by volume of nitrogen, and 35% by volume of steam was passed under conditions of temperature 200° C., pressure 6 kilograms per square centimeter (gauge), and contact time 3.0 seconds, whereupon cis-butene-2 was oxidized. The results are shown in Table 2.

COMPARATIVE EXAMPLE 3

The procedure of Example 13 was repeated wherein ytterbium chloride was not used. The results are shown in Table 2.

TABLE 2

| Run No. | Cis-butene-2 Conversion (mole %) | Methyl Ethyl Ketone Selectivity (mole %) | Methyl Ethyl Ketone Yield (mole %) |
| --- | --- | --- | --- |
| Example 13 | 56 | 60 | 34 |
| Comparative Example 3 | 56 | 46 | 26 |

EXAMPLE 14

A mixture of 7.01 grams of manganese chloride ($MnCl_2 \cdot 4H_2O$), 1.00 gram of rhodium chloride ($RhCl_3 \cdot 3H_2O$), 0.875 gram of ytterbium chloride ($YbCl_3 \cdot 6H_2O$) and 2.44 grams of zinc chloride ($ZnCl_2$) was dissolved in 60 milliliters of water. A γ-alumina carrier molded (specific surface area: 200 square meters per gram; size: 3 millimeters (diameter)×3 millimeters (length)) (39.0 grams) was impregnated with the above-prepared solution which was then vaporized to dryness. The carrier was then calcined at 250° C. for 4 hours in flowing air. There was thus obtained a catalyst supported 1 part by weight of rhodium, 5 parts by weight of manganese, 1 part by weight of ytterbium, and 3 parts by weight of zinc per 100 parts by weight of the carrier.

Twenty milliliters of the above-prepared catalyst was packed into a stainless steel reaction tube (inner diameter: 25 millimeters), through which a mixed gas consisting of 7.5% by volume of butene-1, 7.5% by volume of oxygen, 15% by volume of nitrogen, and 70% by volume of steam was passed continuously under conditions of temperature 180° C., pressure 3 kilograms per square centimeter (gauge), and contact time 3 seconds, whereupon butene-1 was oxidized. The results are shown in Table 3.

REFERENCE EXAMPLE

Butene-1 was oxidized with the same catalyst as used in Example 10 under the same conditions as in Example 13. The results are shown in Table 3.

COMPARATIVE EXAMPLE 4

Butene-1 was oxidized with the same catalyst as used in Comparative Example 2 under the same conditions as in Example 13. The results are shown in Table 3.

TABLE 3

| Run No. | Time from The Start of Reaction (hours) | Butene-1 Conversion (mol %) | Methyl Ethyl Ketone Selectivity (mol %) | Methyl Ethyl Ketone Yield (mol %) |
| --- | --- | --- | --- | --- |
| Example 14 | 10 | 57 | 93 | 53 |
| " | 51 | 49 | 91 | 45 |
| " | 99 | 48 | 90 | 43 |
| Reference Example | 10 | 61 | 83 | 51 |
| Reference Example | 60 | 54 | 76 | 41 |
| Reference Example | 106 | 50 | 70 | 35 |
| Comparative Example 4 | 10 | 66 | 66 | 43 |
| Comparative Example 4 | 54 | 38 | 53 | 20 |
| Comparative Example 4 | 114 | 30 | 47 | 14 |

It can be seen from the above-described results that the three component-base catalyst of the present invention is greatly improved over the prior art rhodium/manganese two component-base catalyst in respect of selectivity of methyl ethyl ketone; that is, the selectivity of methyl ethyl ketone of the catalyst of the present invention is much higher than that of the prior art rhodium/manganese catalyst. Furthermore it can be seen that the four component-base catalyst of the present invention prepared by further adding zinc compounds has a long life time.

What is claimed is:

1. In the process for producing a carbonyl compound by contacting olefin and oxygen or oxygen-containing gas with a catalyst in the presence of water, the improvement which comprises using a catalyst comprising a carrier and (a) rhodium, (b) manganese and (c) a Group IIIA element excluding the actinium series elements.

2. The process of claim 1, wherein the amount of the component (a) is from 0.2 to 5 parts by weight calculated as the rhodium element per 100 parts by weight of the carrier, the amount of the component (b) is from 0.5 to 30 parts by weight calculated as the manganese element per 100 parts by weight of the carrier, and the amount of the component (c) is from 0.1 to 30 parts by weight calculated as the corresponding element per 100 parts by weight of the carrier.

3. The process of claim 1, wherein the carrier is one selected from the group consisting of silica, alumina, silica/alumina, zeolite and activated carbon.

4. In the process for producing a carbonyl compound by contacting olefin and oxygen or oxygen-containing gas with a catalyst in the presence of water, the improvement which comprises using a catalyst comprising a carrier and (a) rhodium, (b) manganese (c) a Group IIIA element excluding the actinium series elements and (d) zinc.

5. The process of claim 4, wherein the amount of the component (a) is from 0.2 to 5 parts by weight calculated as the rhodium element per 100 parts by weight of the carrier, the amount of the component (b) is from 0.5 to 30 parts by weight calculated as the manganese element per 100 parts by weight of the carrier, the amount of the component (c) is from 0.1 to 30 parts by weight calculated as the corresponding element per 100 parts by weight of the carrier, and the amount of the component (d) is from 0.5 to 10 parts by weight calculated as the zinc element per 100 parts by weight of the carrier.

6. The process of claim 4, wherein the carrier is one selected from the group consisting of silica, alumina, silica/alumina, zeolite and activated carbon.

7. The process of claim 1, wherein the olefin is mixed in gas phase with oxygen or oxygen-containing gas and then contacted with the catalyst in the presence of water at a temperature of from 50 to 300° C. under a pressure of from 0 to 50 kilograms per square centimeter (gauge) for 0.1 to 20 seconds.

8. The process of claim 1, wherein the proportions of the olefin:oxygen or oxygen-containing gas: water as vaporized state is 1:0.5–40:1–40 volume ratio.

9. The process of claim 1, wherein rhodium is provided by a rhodium compound selected from the group consisting of halides, sulfates, nitrates, chlorates, acetates, monochloroacetates, oxides and hydroxides.

10. The process of claim 1, wherein manganese is provided by a manganese compound selected from the group consisting of halides, sulfates, nitrates, carbonates, acetates, and oxalates.

11. The process of claim 1, wherein said Group IIIA element is selected from the group consisting of yttrium, scandium, lanthanum, cerium, praseodymium, neodymium, promethium, samarium, europium, gadolinium, terbium, dysprosium, holium, erbium, thulium, ytterbium and lutetium.

12. The process of claim 11, wherein said Group IIIA element is selected from the group consisting of yttrium, praseodymium, neodymium, gadolinium, holmium, erbium and ytterbium.

13. The process according to claim 1, wherein rhodium is provided by rhodium chloride, manganese is provided by manganese chloride and said Group IIIA element is a chloride of yttrium.

14. The process according to claim 12, wherein said Group IIIA element is yttrium.

15. The process according to claim 12, wherein said Group IIIA element is praseodymium.

16. The process according to claim 12, wherein said Group IIIA element is neodymium.

17. The process according to claim 12, wherein said Group IIIA element is gadolinium.

18. The process according to claim 12, wherein said Group IIIA element is holmium.

19. The process according to claim 12, wherein said Group IIIA element is erbium.

20. The process according to claim 12, wherein said Group IIIA element is ytterbium.

21. The process according to claim 3, wherein said carrier is γ-alumina.

22. The process according to claim 21, wherein said γ-alumina is previously treated with hydrochloric acid.

23. The process according to claim 4, wherein rhodium is provided by rhodium chloride, manganese is provided by manganese chloride, the Group IIIA element is ytterbium and is provided by ytterbium chloride and zinc is provided by zinc chloride.

24. The process according to claim 23, wherein said carrier is γ-alumina.

25. The process according to claim 7, wherein said temperature is from 100 to 250° C., said pressure is from 0 to 10 kilograms per square centimeter (gauge) and the time of contact is 1 to 10 seconds.

* * * * *